United States Patent
Wallace et al.

[19]
[11] Patent Number: 6,063,061
[45] Date of Patent: May 16, 2000

[54] FRAGMENTED POLYMERIC COMPOSITIONS AND METHODS FOR THEIR USE

[75] Inventors: Donald G. Wallace, Menlo Park; Cary J. Reich, Los Gatos; Narinder S. Shargill, Dublin; Felix Vega; A. Edward Osawa, both of San Francisco, all of Calif.

[73] Assignee: Fusion Medical Technologies, Inc., Mountain View, Calif.

[21] Appl. No.: 08/903,674

[22] Filed: Jul. 31, 1997

Related U.S. Application Data

[63] Continuation-in-part of application No. 08/704,852, Aug. 27, 1996, abandoned.
[60] Provisional application No. 60/050,437, Jun. 18, 1997.

[51] Int. Cl.7 ...................................................... A61M 5/00
[52] U.S. Cl. ........................................... 604/181; 424/423
[58] Field of Search .................................. 424/423, 445; 514/21; 604/181

[56] References Cited

U.S. PATENT DOCUMENTS

| | | | |
|---|---|---|---|
| 4,013,078 | 3/1977 | Feild | 128/303 |
| 4,453,939 | 6/1984 | Zimmerman et al. | 604/368 |
| 4,554,156 | 11/1985 | Fischer et al. | 424/81 |
| 4,746,514 | 5/1988 | Warne | 424/445 |
| 4,749,689 | 6/1988 | Miyata et al. | 514/21 |
| 4,803,075 | 2/1989 | Wallace et al. | 424/423 |
| 4,891,359 | 1/1990 | Saferstein et al. | 514/21 |
| 5,007,916 | 4/1991 | Linsky et al. | 606/151 |
| 5,017,229 | 5/1991 | Burns et al. | 106/162 |
| 5,061,274 | 10/1991 | Kensey | 606/213 |
| 5,080,893 | 1/1992 | Goldberg et al. | 514/57 |
| 5,108,421 | 4/1992 | Fowler | 606/213 |
| 5,126,141 | 6/1992 | Henry | 424/423 |
| 5,129,882 | 7/1992 | Weldon et al. | 604/96 |
| 5,134,229 | 7/1992 | Saferstein et al. | 536/56 |
| 5,135,751 | 8/1992 | Henry et al. | 424/426 |
| 5,140,016 | 8/1992 | Goldberg et al. | 514/57 |
| 5,149,540 | 9/1992 | Kunihiro | 424/489 |
| 5,192,300 | 3/1993 | Fowler | 606/213 |
| 5,196,185 | 3/1993 | Silver et al. | 424/45 |
| 5,204,382 | 4/1993 | Wallace et al. | 523/115 |
| 5,219,328 | 6/1993 | Morse et al. | 604/49 |
| 5,275,616 | 1/1994 | Fowler | 606/213 |
| 5,330,446 | 7/1994 | Weldon et al. | 604/271 |
| 5,350,573 | 9/1994 | Goldberg et al. | 424/78 |
| 5,352,715 | 10/1994 | WallAce et al. | 523/115 |

(List continued on next page.)

FOREIGN PATENT DOCUMENTS

| | | | |
|---|---|---|---|
| 376931 | 7/1990 | European Pat. Off. | C08L 89/06 |
| WO 86/00912 | 2/1986 | WIPO | C08B 37/00 |
| WO 92/21354 | 12/1992 | WIPO | A61K 31/725 |
| WO 92/22252 | 12/1992 | WIPO | A61B 17/00 |
| WO 95/15747 | 6/1995 | WIPO | A61K 9/16 |
| WO 96/06883 | 3/1996 | WIPO | C08J 3/28 |
| WO 96/39159 | 12/1996 | WIPO | A61K 38/00 |

OTHER PUBLICATIONS

Boyers et al., "Reduction of postoperative pelvic adhesions in the rabbit with Gore–Tex surgical membrane" *Fert. Ster.* (1988) 49(6):1066–1070.

*Primary Examiner*—Michael Buiz
*Assistant Examiner*—Julian W. Woo
*Attorney, Agent, or Firm*—Townsend and Townsend and Crew LLP

[57] ABSTRACT

Molecular cross-linked gels comprise a variety of biologic and non-biologic polymers, such as proteins, polysaccharides, and synthetic polymers. Such molecular gels may be applied to target sites in a patient's body by extruding the gel through an orifice at the target site. Alternatively, the gels may be mechanically disrupted and used in implantable articles, such as breast implants. When used in vivo, the compositions are useful for inhibiting post-surgical spinal and other tissue adhesions, for filling tissue divots, tissue tracts, body cavities, surgical defects, and the like.

31 Claims, 5 Drawing Sheets

U.S. PATENT DOCUMENTS

| | | | |
|---|---|---|---|
| 5,428,024 | 6/1995 | Chu et al. | 514/21 |
| 5,437,672 | 8/1995 | Allyne | 606/61 |
| 5,478,352 | 12/1995 | Fowler | 606/213 |
| 5,507,744 | 4/1996 | Tay et al. | 606/50 |
| 5,516,532 | 5/1996 | Atala et al. | 424/548 |
| 5,531,759 | 7/1996 | Kensey et al. | 606/213 |
| 5,540,715 | 7/1996 | Katsaros et al. | 606/213 |
| 5,599,735 | 1/1997 | Saferstein et al. | 424/94.64 |
| 5,618,551 | 4/1997 | Tardy et al. | 424/426 |
| 5,902,832 | 5/1999 | Van Bladel et al. | 424/423 |

FRAGMENTED POLYMERIC COMPOSITIONS AND METHODS FOR THEIR USE

The present application is a continuation-in-part of provision application Ser. No. 60/050,437, filed on Jun. 18, 1997, and is a continuation-in-part of application Ser. No. 08/704,852, filed on Aug. 27, 1996, abandoned. The full disclosures of both of these applications are incorporated herein by reference.

BACKGROUND OF THE INVENTION

1. Field of the Invention

The present invention relates generally to cross-linked polymeric compositions and to the use of such compositions for inhibiting tissue adhesion and other purposes.

Tissue adhesions occur frequently following surgery and may contribute to or cause compromised surgical results and post-surgical complications. Tissue adhesions may result from unwanted or excessive scar tissue and occur in various body regions including pelvic, abdominal, spinal, tendon, ophthalmic, urinary, thoracic and cardiovascular tissues and are formed when normal tissue bonds to the surfaces of internal organs which have been traumatized or damaged during surgery. Such adhesions may join organs or other body tissues that normally are separate. Treating adhesions may necessitate additional surgery with additional costs, danger and/or discomfort to the patient.

Of particular pertinence to the present application, tissue adhesions often occur after spinal surgery as the result of scar tissue formation between the spinal cord nerves, and adjacent underlying tissues. Such scar tissue formation can compress the nerve roots, producing neural complications such as persistent low back pain and sciatica. At present, peridural scar tissue must be treated with additional surgery.

Numerous procedures and materials have been proposed to minimize or eliminate post-surgical adhesions. Such procedures include introducing barrier materials such as metals, polymers, and natural materials over the target site. A woven material of regenerated cellulose is currently marketed for this purpose by Johnson & Johnson under the trademark Interceed®. This product, however, does not conform well to the underlying tissue. Other polymeric materials that have been tried for this purpose include nylon, cellophane, PTFE, polyethylene, siloxane, elastomers and polylactic acid copolymer films. Many of these materials are not biodegradable and therefore, remain in the body with unpredictable and potentially undesirable consequences.

The reduction and elimination of post-surgical spinal adhesions has been particularly problematic. A variety of permanently implanted devices have been proposed, such as those described in U.S. Pat. Nos. 5,437,672 and 4,013,078. The use of permanent implants, however, is undesirable. The use of resorbable barriers and films has also been proposed. Placement of such barriers and films, however, has also been problematic. The regions between adjacent vertebrae are difficult to access, and it is very difficult to properly place and immobilize barriers and films. The use of non-solid anti-adhesive materials is also problematic since such materials must be sufficiently fluid to enter and conform to the regions being treated, while being sufficiently viscous and persistent so that they remain in the space until the tissue is healed. These objectives must further be balanced with the requirements of biocompatibility and resorbability of the anti-adhesive compositions.

For these reasons, it would be desirable to provide improved compositions, methods, and articles for inhibiting the formation of tissue adhesions following surgery and other trauma. In particular, it would be desirable to provide compositions and methods for introducing such compositions in vivo for the prevention and inhibition of peridural adhesions following laminectomies or other surgical procedures on the spinal column. It would be further desirable if such compositions were useful for the prevention or inhibition of adhesions elsewhere in the body and for other in vivo purposes, such as a filler for tissue voids such as divots resulting from tissue biopsies or other blunt tissue trauma, the filling of implants, such as breast implants, the sealing and/or hemostasis of percutaneous penetrations, and the filling and supplementation of other constrained regions within a patient's body. Moreover, the compositions and methods of the present invention should be adaptable for delivering drugs and other biologically active substances to tissue surfaces adjacent to regions where the compositions have been implanted. At least some of these objectives will be met by the embodiments of the invention of the present application described hereinafter.

2. Description of the Background Art

Barrier films and materials used for preventing or inhibiting spinal and other adhesions are described in U.S. Pat. Nos. 5,350,573, 5,140,016; 5,135,751; 5,134,229; 5,126,141;, 5,080,893; 5,017,229; 5,007,916; PCT publications WO 92/21354; WO 95/15747; WO 86/00912; and Boyers et al. (1988) Fert. Ster. 49: 1066–1070. U.S. Pat. Nos. 5,437,672 and 4,013,078 each describe intervertebral protective devices which remain as permanent implants along the patient's spinal cord.

Collagen and other polymeric plugs intended for sealing percutaneous penetrations, such as tissue tracts created by accessing the femoral artery, are described in a number of patents, including U.S. Pat. Nos. 5,540,715, 5,531,759, 5,478,352; 5,275,616; 5,192,300; 5,108,421; and 5,061,274.

Collagen-containing compositions which have been mechanically disrupted to alter their physical properties are described in U.S. Pat. Nos. 5,428,024; 5,352,715; and 5,204,382. These patents generally relate to fibrillar and insoluble collagens. An injectable collagen composition is described in U.S. Pat. No. 4,803,075. An injectable bone/cartilage composition is described in U.S. Pat. No. 5,516,532. A collagen-based delivery matrix comprising dry particles in the size range from 5 µm to 850 µm which may be suspended in water and which has a particular surface charge density is described in WO 96/39159. A collagen preparation having a particle size from 1 µm to 50 µm useful as an aerosol spray to form a wound dressing is described in U.S. Pat. No. 5,196,185.

A polymeric, non-erodible hydrogel that may be cross-linked and injected via a syringe is described in WO 96/06883. A polyoxyalkylene polymer for inhibiting adhesion is described in U.S. Pat. No. 5,126,141.

The following pending applications, assigned to the assignee of the present application, contain related subject matter: U.S. Ser. No. 60/050,437, filed on Jun. 18, 1997; U.S. Ser. No. 08/704,852, filed on Aug. 27, 1996; U.S. Ser. No. 08/673,710, filed Jun. 19, 1996; U.S. Ser. No. 60/011,898, filed Feb. 20, 1996; U.S. Ser. No. 60/006,321, filed on Nov. 7, 1996; U.S. Ser. No. 60/006,322, filed on Nov. 7, 1996; U.S. Ser. No. 60/006,324, filed on Nov. 7, 1996; and U.S. Ser. No. 08/481,712, filed on Jun. 7, 1995. The full disclosures of each of these applications is incorporated herein by reference.

SUMMARY OF THE INVENTION

The present invention provides improved biocompatible polymeric compositions and methods for applying such compositions at target sites in a patient's body. The methods and compositions will be particularly useful for preventing or inhibiting the formation of tissue adhesions, such as spinal tissue adhesions, following surgery and traumatic injury. In addition, the compositions and methods may also find use in stopping or inhibiting bleeding (hemostasis), particularly when combined with a suitable hemostatic agent, such as thrombin, fibrinogen, clotting factors, and the like. The compositions will be further useful for supplementing tissues, particularly for filling soft and hard tissue regions, including divots, tracts, body cavities, etc., present in muscle, skin, epithelial tissue, connective or supporting tissue, nerve tissue, ophthalmic and other sense organ tissue, vascular and cardiac tissue, gastrointestinal organs and tissue, pleura and other pulmonary tissue, kidney, endocrine glands, male and female reproductive organs, adipose tissue, liver, pancreas, lymph, cartilage, bone, oral tissue, and mucosal tissue. The compositions of the present invention will be still further useful for filling soft implantable devices, such as breast implants, where the material will be protected from degradation by a cellular/enzyme-impermeable barrier or cover. The compositions will additionally be useful in other procedures where it is desirable to fill a confined space with a biocompatible and resorbable polymeric material. Additionally, the compositions may be combined with drugs and other biologically active agents, where the drugs may be released at the target site over time.

The compositions of the present invention comprise a molecular, cross-linked hydrogel which is resorbable and comprises small subunits having a size and other physical properties which enhance the flowability of the gel (e.g. the ability to be extruded through a syringe) and the ability of the gel to flow onto and conform to sites on or in tissue, including tissue surfaces and defined cavities, e.g. intravertebral spaces, tissue divots, holes, pockets, and the like. In particular, the subunits are sized to permit them to flow when the compositions are subjected to stresses above a threshold level, for example when extruded through an orifice or cannula or when packed into a delivery site using a spatula, or the like. The threshold stresses are typically in the range from $3 \times 10^4$ Pa to $5 \times 10^5$ Pa. The compositions, however, will remain generally immobile when subjected to stresses below the threshold level.

The compositions may be dry, partially hydrated or fully hydrated and will display a degree of swelling from 0% to 100%, depending on the extent of hydration. The fully hydrated material will absorb from about 400% to about 1300% water or aqueous buffer by weight, corresponding to a nominal increase in diameter or width of an individual particle of subunit in the range from approximately 50% to approximately 500%, usually from approximately 50% to approximately 250%. Thus, the size of particles in the dry powder starting material (prior to hydration) will be determine the partially or fully hydrated size of the subunit (depending on the factors described below). Exemplary and preferred size ranges for the dry particles and fully hydrated subunits are as follows:

Particle/Subunit Size

|  | Exemplary Range | Preferred Range |
| --- | --- | --- |
| Dry Particle | 0.01 mm–1.5 mm | 0.05 mm–1 mm |
| Fully Hydrated Hydrogel Subunit | 0.05 mm–3 mm | 0.25 mm–1.5 mm |

Compositions of the present invention will usually be in the form of a dry powder, a partially hydrated gel, or a fully hydrated gel. The dry powder (having a moisture content below 20% by weight) will be useful as a starting material for preparation of the hydrogels, as described below. The partially hydrated gels, typically having from 50% to 80% hydration, are useful for applications where it is desired that the material further swell upon application to a moist target site, e.g. a tissue divot. The fully hydrated forms will be useful for applications where in situ swelling is not desired, such as in the spinal column and other areas where nerves and other sensitive structures are present.

The dimensions of the subunits may be achieved in a variety of ways. For example, a cross-linked hydrogel having dimensions larger than the target range (as defined below) may be mechanically disrupted at a variety of points during the production process. In particular, the composition may be disrupted (1) before or after cross-linking of a polymer starting material and (2) before or after hydration of the cross-linked or non-cross-linked polymer starting material, e.g. as a fully or partially hydrated material or as a dry particulate powder. The term "dry" will mean that the moisture content is sufficiently low, typically below 20% by weight water, so that the powder will be free-flowing and that the individual particles will not aggregate. The term "hydrated" will mean that the moisture content is sufficiently high, typically above 50% of the equilibrium hydration level, usually in the range from 80% to 95% of the equilibrium hydration level, so that the material will act as a hydrogel.

Mechanical disruption of the polymer material in the dry state is preferred in cases where it is desired to control the particle size and/or particle size distribution. It is easier to control comminution of the dry particles than the hydrated hydrogel materials, and the size of the resulting reduced particles is thus easier to adjust. Conversely, mechanical disruption of the hydrated, cross-linked hydrogels is generally simpler and involves fewer steps than does commination of a dry polymer starting material. Thus, the disruption of hydrated gels may be preferred when the ultimate gel subunit size and/or size distribution is not critical.

In a first exemplary production process, a dry, non-cross-linked polymer starting material, e.g. dry gelatin powder, is mechanically disrupted by a conventional unit operation, such as homogenization, grinding, coacervation, milling, jet milling, and the like. The powder will be disrupted sufficiently to achieve dry particle sizes which produce hydrogel subunit sizes in the desired ranges when the product is partially or fully hydrated. The relationship between the dry particle size and the fully hydrated subunit size will depend on the swellability of the polymeric material, as defined further below.

Alternatively, a particulate polymeric starting material may be formed by spray drying. Spray drying processes rely on flowing a solution through a small orifice, such as a nozzle, to form droplets which are released into a counter-current or co-current gas stream, typically a heated gas stream. The gas evaporates solvent from the liquid starting material, which may be a solution, dispersion, or the like. Use of spray drying to form a dry powder starting material is an alternative to mechanical disruption of the starting material. The spray drying operation will usually produce a non-cross-linked dry powder product with a highly uniform particle size. The particles may then be cross-linked, as described below.

In many instances, the mechanical disruption operation can be controlled sufficiently to obtain both the particle size and particle size distribution within a desired range. In other cases, however, where more precise particle size distributions are required, the disrupted material can be further treated or selected to provide the desired particle size distribution, e.g. by sieving, aggregation, or the like. The mechanically disrupted polymeric starting material is then cross-linked as described in more detail below, and dried. The dried material may be the desired final product, where it may be rehydrated and swollen immediately prior to use. Alternatively, the mechanically disrupted, cross-linked material may be rehydrated, and the rehydrated material packaged for storage and subsequent use. Particular methods for packaging and using these materials are described below.

Where the subunit size of the fragmented hydrogel is less important, the dried polymeric starting material may be hydrated, dissolved, or suspended in a suitable buffer and cross-linked prior to mechanical disruption. Mechanical disruption of the pre-formed hydrogel will typically be achieved by passing the hydrogel through an orifice, where the size of the orifice and force of extrusion together determine the particle size and particle size distribution. While this method is often operationally simpler than the mechanical disruption of dry polymeric particles prior to hydration and cross-linking, the ability to control the gel particle size is much less precise.

In a particular aspect of the mechanical disruption of pre-formed gels, the gels may be packed in a syringe or other applicator prior to mechanical disruption. The materials will then be mechanically disrupted as they are applied through the syringe to the tissue target site, as discussed in more detail below. Alternatively, a non-disrupted, cross-linked polymeric material may be stored in a dry form prior to use. The dry material may then be loaded into a syringe or other suitable applicator, hydrated within the applicator, and mechanically disrupted as the material is delivered to the target site, again typically being through an orifice or small tubular lumen.

The polymer will be capable of being cross-linked and of being hydrated to form a hydrogel, as described in more detail below. Exemplary polymers include proteins selected from gelatin, collagen (e.g. soluble collagen), albumin, hemoglobin, fibrinogen, fibrin, fibronectin, elastin, keratin, laminin, and derivatives and combinations thereof. Alternatively, the polymer may comprise a polysaccharide, such as a glycosaminoglycan, a starch derivative, a cellulose derivative, a hemicellulose derivative, xylan, agarose, alginate, chitosan, and combinations thereof. As a further alternative, the polymer may comprise a non-biologic hydrogel-forming polymer, such as polyacrylates, polymethacrylates, polyacrylamides, polyvinyl polymers, polylactide-glycolides, polycaprolactones, polyoxyethylenes, and derivatives and combinations thereof.

Cross-linking of the polymer may be achieved in any conventional manner. For example, in the case of proteins, cross-linking may be achieved using a suitable cross-linking agent, such as an aldehyde, sodium periodate, epoxy compounds, and the like. Alternatively, cross-linking may be induced by exposure to radiation, such as γ-radiation or electron beam radiation. Polysaccharides and non-biologic polymers may also be cross-linked using suitable cross-linking agents and radiation. Additionally, non-biologic polymers may be synthesized as cross-linked polymers and copolymers. For example, reactions between mono- and poly-unsaturated monomers can result in synthetic polymers having controlled degrees of cross-linking. Typically, the polymer molecules will each have a molecular weight in the range from 20 kD to 200 kD, and will have at least one link to another polymer molecule in the network, often having from 1 to 5 links, where the actual level of cross-linking is selected in part to provide a desired rate of biodegradability in the ranges set forth below.

The extent of cross-linking of the polymer has an effect on several functional properties of the hydrogel including extrudability, absorptiveness of surrounding biological fluids, cohesiveness, ability to fill space, swelling ability and ability to adhere to the tissue site. The extent of cross-linking of the polymeric gel composition may be controlled by adjusting the concentration of cross-linking agent, controlling exposure to cross-linking radiation, changing the relative amounts of mono- and poly-unsaturated monomers, varying reaction conditions, and the like. Typically, the degree of cross-linking is controlled by adjusting the concentration of cross-linking agent.

Exposure to radiation, such as γ-radiation, may also be carried out in order to sterilize the compositions before or after packaging. When the compositions are composed of radiation-sensitive materials, it will be necessary to protect the compositions from the sterilizing radiation. For example, in some cases, it will be desirable to add ascorbic acid in order to inhibit further cross-linking of the materials from free radical mechanisms.

The hydrogel compositions of the present invention will typically have a solids content in the range from 1% by weight to 70% by weight, preferably from 5% by weight to 20% by weight, preferably from 5% by weight to 16% by weight. For gels having a higher solid content, typically above 16% by weight, it is preferred to include a plasticizer in the composition, typically from 0.1% by weight to 30% by weight, preferably from 1% by weight to 5% by weight. Suitable plasticizers include polyethylene glycols, sorbitol, glycerol, and the like.

The equilibrium swell of the cross-linked polymers of the present invention will generally range from 400% to 1300%, preferably being from 500% to 1100%, depending on its intended use. Such equilibrium swell may be controlled by varying the degree of cross-linking, which in turn is achieved by varying the cross-linking conditions, such as the type of cross-linking method, duration of exposure of a cross-linking agent, concentration of a cross-linking agent, cross-linking temperature, and the like.

Materials having equilibrium swell values from about 400% to 1300% were prepared and are described in the Experimental section hereinafter. It was found that materials having differing equilibrium swell values perform differently in different applications. For example, the ability to inhibit bleeding in a liver divot model was most readily achieved with cross-linked gelatin materials having a swell in the range from 700% to 950%. For a femoral artery plug, lower equilibrium swell values in the range from 500% to 600% were more successful. Thus, the ability to control cross-linking and equilibrium swell allows the compositions of the present invention to be optimized for a variety of uses.

In addition to equilibrium swell, it is also important to control the hydration of the material immediately prior to delivery to a target site. Hydration and equilibrium swell are, of course, intimately connected. A material with 0% hydration will be non-swollen. A material with 100% hydration will be at its equilibrium water content. Hydrations between 0% and 100% will correspond to swelling between the minimum and maximum amounts. As a practical matter, many dry, non-swollen materials according to the present invention will have some residual moisture content, usually below 20% by weight, more usually from 8% to 15% by weight. When the term "dry" is used herein, it will specify materials having a low moisture content where the individual particles are free flowing and generally non-swollen.

Hydration can be adjusted very simply by controlling the amount of aqueous buffer added to a dry or partially hydrated cross-linked material prior to use. Usually, at a minimum, it will be desirable to introduce sufficient aqueous buffer to permit extrusion through a syringe or other delivery device. In other cases, however, it may be desirable to utilize a spatula or other applicator for delivering less fluid materials. The intended use will also help determine the desired degree of hydration. In cases where it is desired to fill or seal a moist cavity, it is generally desirable to employ a partially hydrated gel which can swell and fill the cavity by absorbing moisture from the target site. Conversely, fully or substantially fully hydrated gels are preferred for application in the brain, near the spine, and to target sites near nerves and other sensitive body structures which could be damaged by post-placement swelling. It would also be possible to prepare the gel compositions of the present invention with excess buffer, resulting in a two-phase composition having a fully hydrated gel and a free buffer phase.

A preferred hydrogel material according to the present invention is a gelatin which has been cross-linked to achieve from 700% to 950% swell at equilibrium hydration. The material will be disrupted to have a gel particle size in the range from 0.01 mm to 1.5 mm, preferably 0.05 mm to 0.5 mm, and will preferably be hydrated at a level sufficient to achieve 70% to 100% of the equilibrium swell prior to application to the site.

In some cases, the hydrogel compositions of the present invention may contain a combination of two or more different materials, e.g combinations of proteins and polysaccharides and/or non-biologic polymers, as well as combinations of two or more individual materials from each of the polymer types, e.g. two or more proteins, polysaccharides, etc.

The polymeric compositions of the present invention may also comprise combinations of the disrupted, cross-linked polymer hydrogels described above and non-cross-linked polymeric materials. The disrupted, cross-linked polymeric hydrogels consist of a plurality of subunits having a size determined by preparation method. The size is selected to be useful for packing a confined volume, having both the flowability and the rate of biodegradability described below. The discrete nature of the cross-linked subunits, however, will leave void areas which may be filled by combination with a non-cross-linked polymeric material. The non-cross-linked polymeric or other filler material may comprise any of the polymeric materials listed above, and may optionally but not necessarily be the same polymeric material which has been cross-linked to form the cross-linked mechanically disrupted gel. The relative amounts of cross-linked polymer and non-cross-linked polymer will be selected to provide a relatively continuous (free of voids) composition after optional mechanical disruption and delivery to a target site, typically having a weight ratio in the range from 20:1 to 1:1 (cross-linked polymer:non-cross-linked polymer), usually in the range from 10:1 to 2:1, preferably from 5:1 to 2:1.

The hydrogels of the present application may be applied using a syringe, a spatula, a brush, a spray, manually by pressure, or by any other conventional technique. Usually, the gels will be applied using a syringe or similar applicator capable of extruding the gel through an orifice, aperture, needle, tube, or other passage to form a bead, layer, or similar portion of material. Mechanical disruption of the gels can occur as the gel is extruded through an orifice in the syringe or other applicator, typically having a size in the range from 0.01 mm to 5.0 mm, preferably 0.5 mm to 2.5 mm. Preferably, however, the polymeric hydrogel will be initially prepared from a powder having a desired particle size (which upon hydration yields hydrogel subunits of the requisite size) or will be partially or entirely mechanically disrupted to the requisite size prior to a final extrusion or other application step.

The compositions may be applied at varying degrees of hydration, usually but not necessarily being at least partially hydrated. If applied in a non-hydrated form, the compositions will swell to their full equilibrium swell value, i.e. from about 400% to about 1300% as set forth above. When applied at their full hydration, the compositions will display substantially equilibrium hydration and little or no swelling when applied to tissue. Swelling of the non-hydrated and partially hydrated compositions results from absorption of moisture from the tissue and surroundings to which the composition is being applied.

The present invention still further provides kits comprising any of the hydrated or non-hydrated gel materials described above in combination with written instructions for use (IFU) which set forth any of the methods described above for applying the gel onto a target site on tissue. The composition and written instructions will be included together in a conventional container, such as a box, jar, pouch, tray, or the like. The written instructions may be printed on a separate sheet of paper or other material and packaged on or within the container or may be printed on the container itself. Usually, the composition(s) will be provided in a separate, sterile bottle, jar, vial, or the like. When the gel material is non-hydrated, the kit may optionally include a separate container with a suitable aqueous buffer for hydration. Other system components such as the applicator, e.g. syringe, may also be provided.

DESCRIPTION OF THE SPECIFIC EMBODIMENTS

Figure 1:
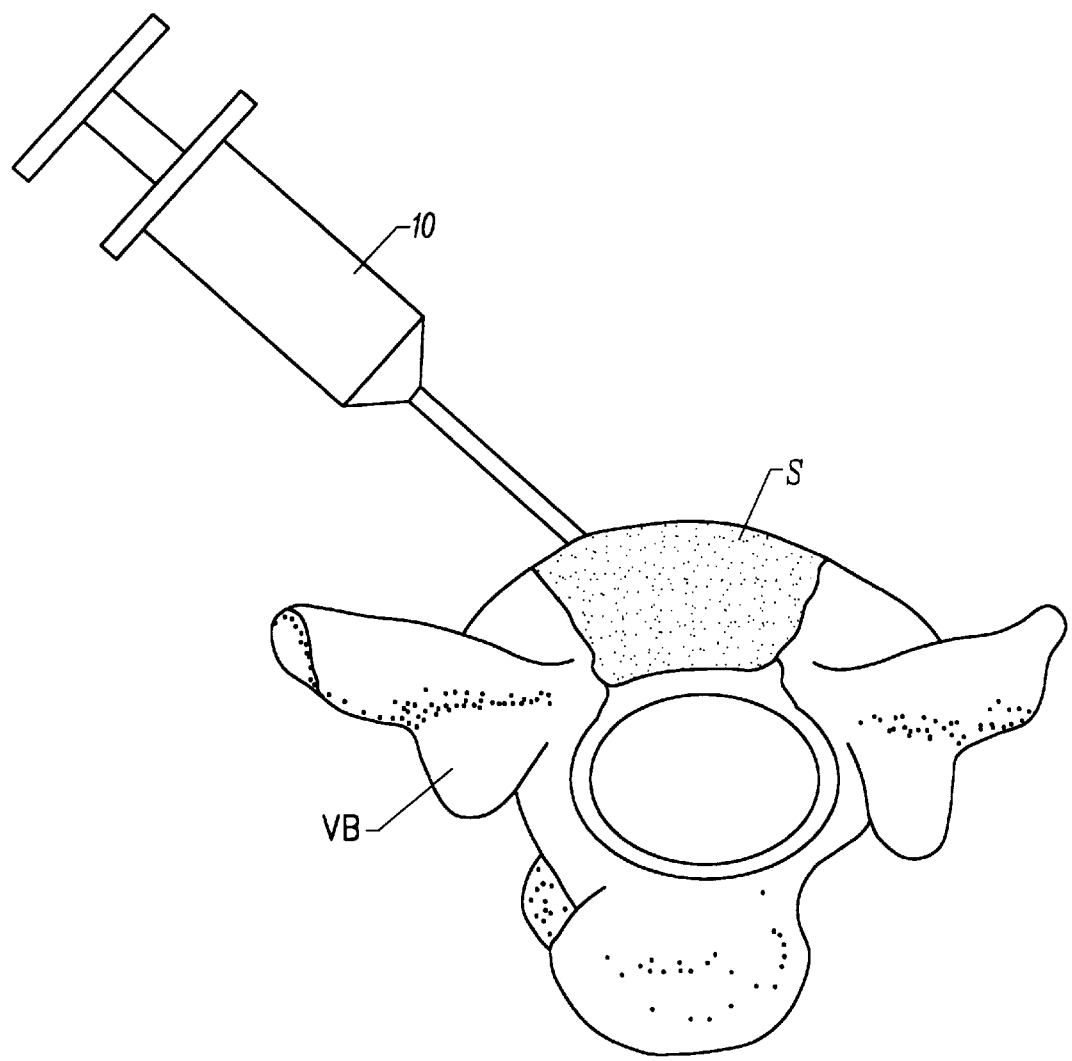
FIG. 1 illustrates the application of the molecular cross-linked polymeric gel of the present invention to a surgically created defect in the vertebral body for preventing post-surgical spinal adhesions.

Compositions according to the present invention comprise resorbable biocompatible molecular cross-linked hydrogels. By "biocompatible" is meant that the materials will meet the criteria in standard # ISO 10993-1 promulgated by the International Organization for Standardization (NAMSA, Northwood, Ohio). By "resorbable," it is meant that the compositions will degrade or solubilize, when placed directly into a target site in a patient's body (and not protected within an implant device such as a breast implant), over a time period of less than one year, usually from 1 to 120 days. A particular protocol for measuring resorption and degradation is set forth in the Experimental section hereinafter. By "molecular cross-linked", it is meant that the materials comprise polymer molecules (i.e. individual chains) which are attached by bridges composed of either an element, a group, or a compound, where the backbone atoms of the polymer molecules are joined by primary chemical bonds. Cross-linking may be effected in a variety of ways, as will be described in greater detail below.

By "hydrogel," it is meant that the composition comprises a single phase aqueous colloid in which a biologic or non-biologic polymer, as defined in more detail below, absorbs water or an aqueous buffer. The hydrogel comprises multiple sub-networks, where each sub-network is a molecular cross-linked hydrogel having dimensions which depend on the degree of hydration and are within the ranges set forth above. Preferably, the hydrogels will have little or no free water, i.e. water cannot be removed from the hydrogel by simple filtration.

By "percent swell," it is meant that the dry weight is subtracted from the wet weight, divided by the dry weight and multiplied by 100, where wet weight is measured after the wetting agent has been removed as completely as possible from the exterior of the material, e.g. by filtration, and where dry weight is measured after exposure to an elevated temperature for a time sufficient evaporate the wetting agent, e.g., 2 hours at 120° C.

"Equilibrium swell," is defined as the percent swell at equilibrium after the polymeric material has been immersed in a wetting agent for a time period sufficient for water content to become constant, typically 18 to 24 hours.

"Target site" is the location to which the gel material is to be delivered. Usually, the target site will be the tissue location of interest, but in some cases the gel may be administered or dispensed to a location near the location of interest, e.g. when the material swells in situ to cover the location of interest.

The hydrogels of the present invention may be formed from biologic and non-biologic polymers. Suitable biologic polymers include proteins, such as gelatin, soluble collagen, albumin, hemoglobin, casein, fibrinogen, fibrin, fibronectin, elastin, keratin, laminin, and derivatives and combinations thereof. Particularly preferred is the use of gelatin or soluble non-fibrillar collagen, more preferably gelatin, and exemplary gelatin formulations are set forth below. Other suitable biologic polymers include polysaccharides, such as glycosaminoglycans, starch derivatives, xylan, cellulose derivatives, hemicellulose derivatives, agarose, alginate, chitosan, and derivatives and combinations thereof. Suitable non-biologic polymers will be selected to be degradable by either of two mechanisms, i.e. (1) break down of the polymeric backbone or (2) degradation of side chains which result in aqueous solubility. Exemplary nonbiologic hydrogel-forming polymers include synthetics, such as polyacrylates, polymethacrylates, polyacrylamides, polyvinyl resins, polylactide-glycolides, polycaprolactones, polyoxyethylenes, and derivatives and combinations thereof.

The polymer molecules may be cross-linked in any manner suitable to form an aqueous hydrogel according to the present invention. For example, polymeric molecules may be cross-linked using bi- or poly-functional cross-linking agents which covalently attach to two or more polymer molecules chains. Exemplary bifunctional cross-linking agents include aldehydes, epoxies, succinimides, carbodiimides, maleimides, azides, carbonates, isocyanates, divinyl sulfone, alcohols, amines, imidates, anhydrides, halides, silanes, diazoacetate, aziridines, and the like. Alternatively, cross-linking may be achieved by using oxidizing and other agents, such as periodates, which activate side-chains or moieties on the polymer so that they may react with other side-chains or moieties to form the cross-linking bonds. An additional method of cross-linking comprises exposing the polymers to radiation, such as gamma radiation, to activate the side polymer to permit cross-linking reactions. Dehydrothermal cross-linking methods would also be suitable. Dehydrothermal cross-linking of gelatin can be achieved by holding it at an elevated temperature, typically 120° C., for a period of at least 8 hours. Increasing the extent of cross-linking, as manifested in a decline in percent swell at equilibrium, can be achieved by elevating the holding temperature, extending the duration of the holding time, or a combination of both. Operating under reduced pressure can accelerate the cross-linking reaction. Preferred methods for cross-linking gelatin molecules are described below.

Optionally, the molecular cross-linked hydrogel may include a plasticizer to increase the malleability, flexibility, and rate of degradation of the gel. The plasticizer may be an alcohol, such as polyethylene glycol, sorbitol, or glycerol, preferably being polyethylene glycol having a molecular weight ranging from about 200 to 1000 D, preferably being about 400 D. The plasticizers will be present in the compositions at from about 0.1% by weight to about 30% by weight, preferably from 1% by weight to 5% by weight of the composition. The plasticizers are particularly beneficial for use with gels having a high solids content, typically above 10% by weight of the composition (without plasticizer).

Exemplary methods for producing molecular cross-linked gelatins are as follows. Gelatin is obtained and placed in an aqueous buffer to form a non-cross-linked gel, typically having a solids content from 1% to 70% by weight, usually from 3% to 10% by weight. The gelatin is cross-linked, typically by exposure to either glutaraldehyde (e.g. 0.01% to 0.05% w/w, overnight at 0°–8° C. in aqueous buffer), sodium periodate (e.g. 0.05 M, held at 0° C. to 8° C. for 48 hours) or 1-ethyl-3-(3-dimethylaminopropyl) carbodiimide ("EDC") (e.g., 0.5% to 1.5% w/w, overnight at room temperature), or by exposure to about 0.3 to 3 megarads of gamma or electron beam radiation. Alternatively, gelatin particles can be suspended in an alcohol, preferably methyl alcohol or ethyl alcohol, at a solids content of 1% to 70% by weight, usually 3% to 10% by weight, and cross-linked by exposure to a cross-linking agent, typically glutaraldehyde (e.g., 0.01% to 0.1% w/w, overnight at room temperature). When cross-linking with glutaraldehyde, the cross-links are formed via Schiff bases which may be stabilized by subsequent treatment with sodium borohydride. In the case of aldehydes, the pH should be held from about 6 to 11, preferably from 7 to 10. After cross-linking, the resulting granules may be washed in distilled water and optionally rinsed in an alcohol, dried and resuspended to a desired degree of hydration in an aqueous medium having a desired buffer and pH. The resulting hydrogels may then be loaded into the applicators of the present invention, as described in more detail hereinafter. Alternatively, the hydrogels may be mechanically disrupted prior to or after cross-linking, also as described in more detail hereinafter.

Exemplary methods for producing molecular cross-linked gelatin compositions having equilibrium percent swells in the range from about 400% to about 1300%, preferably 600% to 950%, are as follows. Gelatin is obtained and placed in an aqueous buffer (typically at a pH of 6 to 17, preferably at a pH between 7 and 10) containing a cross-linking agent in solution (typically glutaraldehyde, preferably at a concentration of 0.01% to 0.1% w/w) to form a gel, typically having a solids content from 1% to 70% by weight, usually from 3% to 10% by weight. The gel is well mixed and held overnight at 0°–8° C. as cross-linking takes place. It is then rinsed three times with deionized water, twice with an alcohol (preferably methyl alcohol, ethyl alcohol, or isopropyl alcohol) and allowed to dry at room temperature. Optionally, the gel may be treated with sodium borohydride to further stabilize the cross-linking.

The compositions of the present invention may be further combined with other materials and components, such as bioactive component(s) to be delivered to the patient, viscosity modifiers, such as carbohydrates and alcohols, and other materials intended for other purposes, such as to control the rate of resorption. Exemplary bioactive components include, but are not limited to, proteins, carbohydrates, nucleic acids, and inorganic and organic biologically active molecules such as enzymes, antibiotics, antineoplastic agents, bacteriostatic agents, bacteriocidal agents, antiviral agents, hemostatic agents, local anesthetics, anti-inflammatory agents, hormones, antiangiogenic agents, antibodies, neurotransmitters, psychoactive drugs, drugs affecting reproductive organs and oligonucleotides, such as antisense oligonucleotides. Such bioactive components will typically be present at relatively low concentrations, typically below 10% by weight of the compositions, usually below 5% by weight, and often below 1% by weight.

Exemplary hemostatic agents include thrombin, fibrinogen and clotting factors. Hemostatic agents like thrombin may be added in concentrations ranging from 50 to 10,000 Units thrombin per ml gel, preferably from about 100 Units thrombin per ml gel to about 1000 Units thrombin per ml gel.

The molecular cross-linked hydrogels of the present invention can be mechanically disrupted at the time they are delivered to a target site by extrusion through an orifice or other flow restriction, or they can be mechanically disrupted in a batch process prior to delivery to a target site. The primary purpose of this mechanical disruption step is to create multiple subunits of hydrogel having a size which enhances the ability to fill and pack the space to which it is being delivered. Another purpose of the mechanical disruption is to facilitate passage of the gel down small diameter tubes, cannulas, and/or other applicators to the target site. Without mechanical disruption, the molecular cross-linked hydrogels will have difficulty conforming to and filling the irregularly target spaces which are being treated, e.g. intravertebral spaces in the spinal column, tissue divots, percutaneous tissue tracks, and the like. By breaking the gel down to smaller sized sub-units, such spaces can be filled much more efficiently while retaining the mechanical integrity and persistence of the cross-linked gel which are essential for it to act as an anti-adhesive agent, tissue filler, or the like. Surprisingly, it has been found that a single manual extrusion of the composition, typically using a syringe having an orifice in size in the range from 0.01 mm to 5.0 mm, preferably from 0.1 mm to 2.5 mm, provides the proper amount of mechanical disruption to enhance the gel properties as described above.

Alternatively, the gel compositions of the present invention may be mechanically disrupted prior to their final use or delivery. Molecular cross-linking of the polymer chains of the gel can be performed before or after its mechanical disruption. The gels may be mechanically disrupted in batch operations, such as mixing, so long as the gel composition is broken down into sub-units having a size in the 0.01 mm to 5.0 mm range set forth above. When the gel composition is disrupted prior to use, the gel can be applied or administered by techniques other than extrusion e.g. using a spatula, spoon, or the like. Other batch mechanical disruption processes include pumping through a homogenizer or mixer or through a pump which compresses, stretches, or shears the gel to a level which exceeds a fractural yield stress of the hydrogel. In some cases, extrusion of the polymeric composition causes the gel to be converted from a substantially continuous network, i.e. a network which spans the dimensions of the original gel mass, to a collection of sub-networks or sub-units having dimensions in the ranges set forth above. In other cases it may be desirable to partially disrupt the gel compositions prior to packaging in the syringe or other applicator. In such cases, the gel material will achieve the desired sub-unit size prior to final extrusion.

In a presently preferred embodiment, the polymer may be initially prepared (e.g. by spray drying) and/or be mechanically disrupted prior to being cross-linked, often usually prior to hydration to form a gel. The polymer may be provided as a finely divided or powdered dry solid which may be disrupted by further comminution to provide particles having a desired size, usually being narrowly confined within a small range. Further size selection and modification steps, such as sieving, cyclone classification, etc., may also be performed. For the exemplary gelatin materials described hereinafter, the dry particle size is preferably in the range from 0.01 mm to 1.5 mm, more preferably from 0.05 mm to 1.0 mm. An exemplary particle size distribution will be such that greater than 950% by weight of the particles are in the range from 0.05 mm to 0.7 mm. Methods for comminuting the polymeric starting material include homogenization, grinding, coacervation, milling, jet milling, and the like. Powdered polymeric starting materials may also be formed by spray drying. The particle size distribution may be further controlled and refined by conventional techniques such as sieving, aggregation, further grinding, and the like.

The dry powdered solid may then be suspended in an aqueous buffer, as described elsewhere herein, and cross-linked. In other cases, the polymer may be suspended in an aqueous buffer, cross-linked, and then dried. The cross-linked, dried polymer may then be disrupted, and the disrupted material subsequently resuspend in an aqueous buffer. In all the cases, the resulting material comprises a cross-linked hydrogel having discrete sub-networks having the dimensions set forth above.

The compositions of the present invention, after mechanical disruption, will be resorbable, i.e., they will biodegrade in the patient's body, in a period of less than one year, usually from 1 to 120 days, preferably from 1 to 90 days, and more preferably from 2 to 30 days following their initial application. This is particularly true when the materials are used for preventing post-surgical and other adhesions, where a barrier is necessary between the healing tissue surfaces only for so long as the tissue is healing. Techniques for measuring the length of time required for resorption are set forth in Example 11 in the Experimental section below. In other cases, such as when the compositions are contained within an implantable device, such as a breast implant, resorption of the material will be prevented by the membrane or other mechanical barrier surrounding the compositions (unless the integrity of the barrier is broken).

Referring now to FIG. 1, a method for preventing adhesions following a laminectomy procedure will be described. A syringe 10 containing the resorbable molecular cross-linked gel of the present invention is used to apply the gel in such a manner that all exposed dura is covered. Usually, the gel will be resorbed over a time period in the range from 7 to 60 days.

Figure 2A:
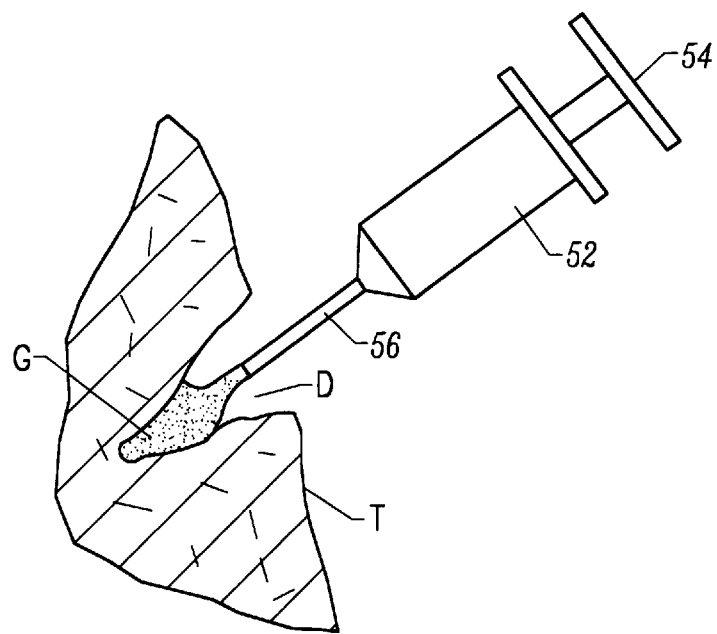
FIGS. 2A and 2B illustrate application of the molecular cross-linked polymeric gel compositions of the present invention to a defect in soft tissue, where the treated region is optionally covered with a protective patch after the defect is filled with the polymeric composition.
Figure 2B:
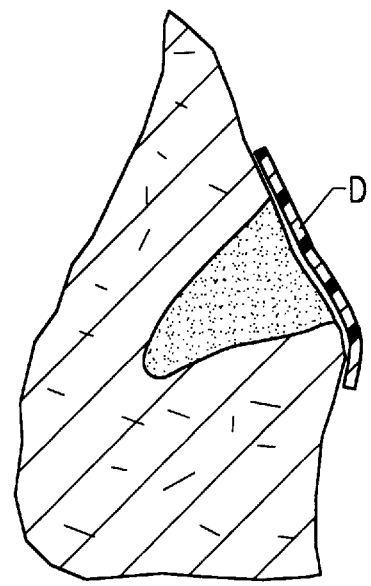

Referring now to FIGS. 2A and 2B, the molecular cross-linked hydrogels of the present invention may also be used to fill divots D in soft tissue T. A syringe 50 comprising a barrel 52, plunger 54 and cannula 56 contains the molecular cross-linked hydrogel in the interior of the barrel 52. The hydrogel G is extruded through the cannula 56 by depressing the plunger 54 in a conventional manner. Sufficient gel is extruded to fill the divot, as shown in FIG. 2B. Preferably, a partially hydrated hydrogel which will swell further upon exposure to the moist tissue environment will be used. It may be desirable to place a patch P over the exposed surface of the gel, as shown in FIG. 2B. The patch may be an adhesive or other conventional self-securing patch. Preferably, however, the patch comprises a collagen, gelatin, or other film that may be immobilized by applying energy e.g. optical or radio frequency energy as described in published PCT applications WO 96/07355 and WO 92/14513.

Figure 3A:
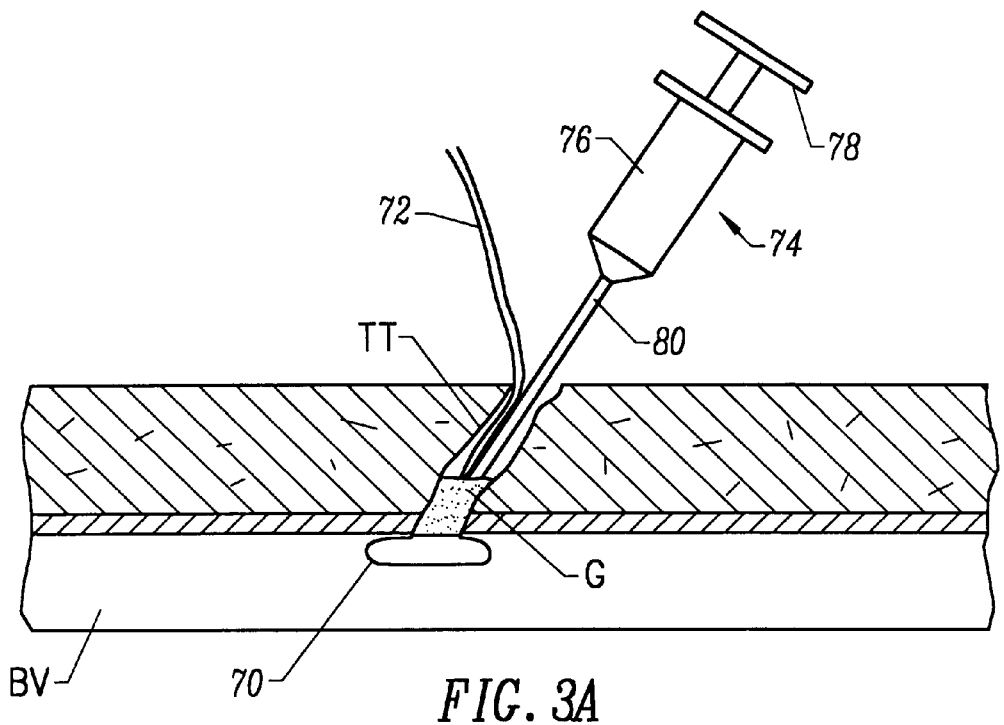
FIGS. 3A and 3B illustrate use of the molecular cross-linked polymeric compositions of the present invention for filling a percutaneous tissue penetration to a blood vessel, such as a tissue tract formed as part of an intravascular catheterization procedure.
Figure 3B:
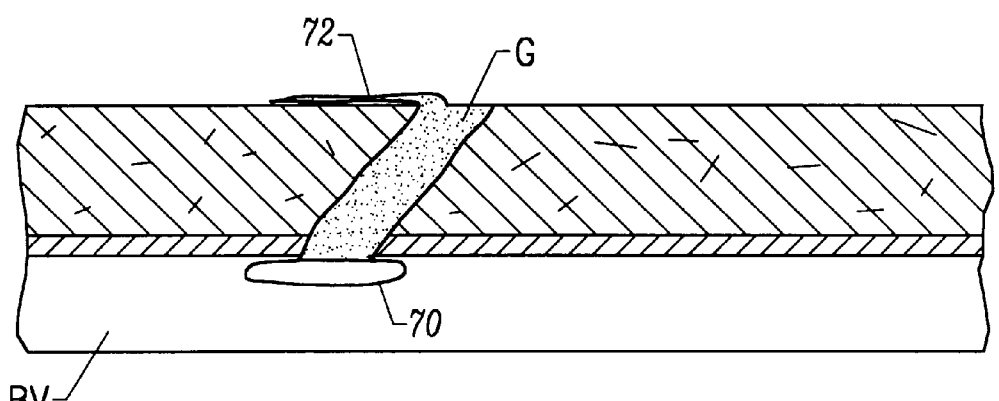

Referring now to FIGS. 3A and 3B, compositions and methods of the present invention may also be used to fill percutaneous tissue tracts TT which were formed through overlying tissue to access blood vessels BV. A barrier element 70 may be placed along the inner wall of the blood vessel at the distal end of the tissue tract TT. Filament 72 may be used to hold the barrier element 70 in place. A syringe 74 comprising a barrel 76, plunger 78, and cannula 80 is then used to extrude the molecular cross-linked hydrogel material of the present invention into the tissue tract over the barrier element 70. The hydrogel G will be used to fill the entire interior volume of the tissue tract TT, as shown in FIG. 3B, and will preferably be partially hydrated to permit post-placement swelling as described above. Optionally, a patch or other cover may be placed over the exposed surface of the tissue tract (not shown). The barrier element 70 may then be removed.

Figure 4:
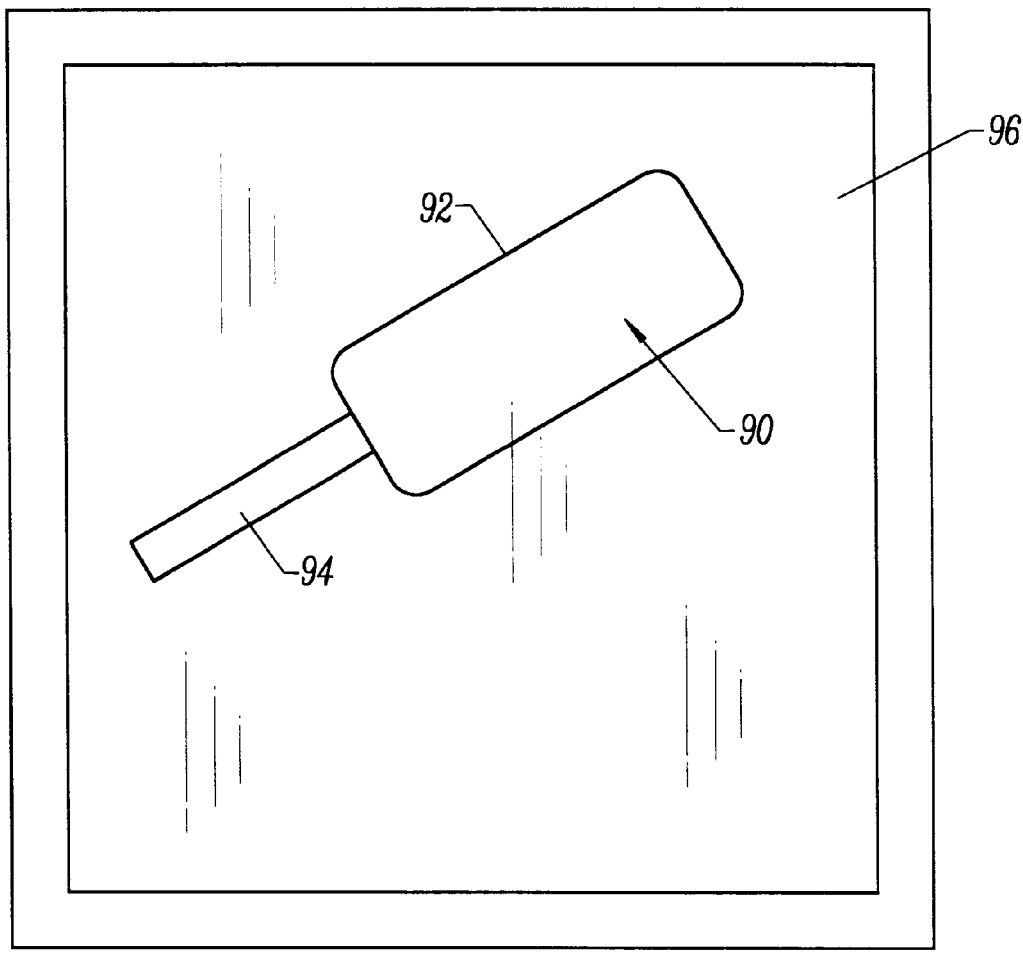
FIG. 4 illustrates a kit comprising a sterile package for an applicator containing the molecular cross-linked polymeric composition of the present invention.
Figure 5:
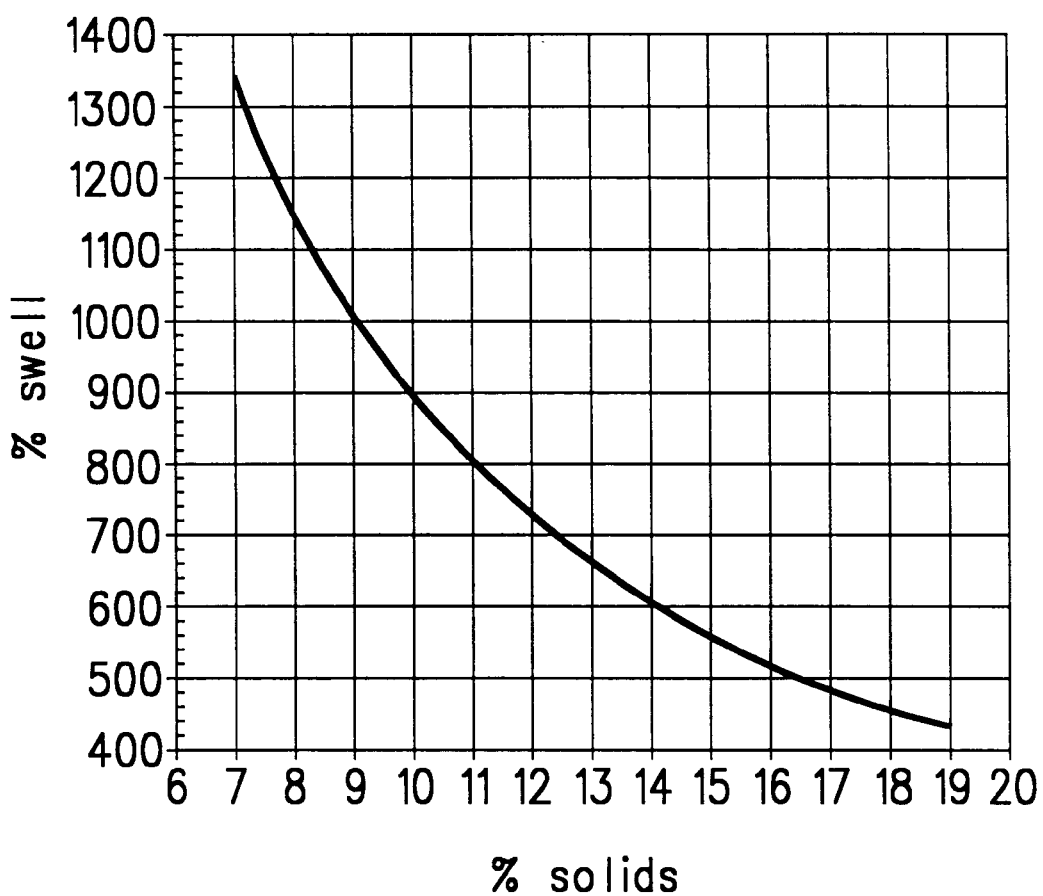
FIG. 5 illustrates the correlation between percent swell and the percent solids of the polymeric gel.

Referring now to FIG. 4, the present invention comprises kits including the hydrated, partially hydrated, and/or non-hydrated polymeric compositions described above packaged in a suitable container, usually with written instructions for use. For example, the composition may be packaged in an applicator 90 which contains the pre-extruded molecular cross-linked hydrogel of the present invention. The applicator may take a wide variety of forms, including syringes as previously described. In FIG. 4, the applicator 90 comprises a tube 92 having a neck 94 which defines an extrusion orifice. The gel is contained within the tube and may be extruded through the neck 94 by squeezing the tube. The applicator 90 is preferably contained in a sterile package 96. The sterile package may take a variety of forms, and is illustrated as an envelope comprising a backing sheet and a clear plastic cover. Such packages may be sterilized in a conventional manner. Optionally, the radiation used to cross-link the hydrogel may also be used to sterilize the entire package. The instructions for use may be printed on the packaging or provided on a separate sheet placed in the package.

The present invention may also be used to inhibit bleeding (cause hemostasis) on an abraded or damaged tissue surface, e.g., any organ surface including the liver, spleen, heart, kidney, intestine, blood vessels, vascular organs, and the like. A syringe containing the resorbable molecular cross-linked gel combined with a hemostasis agent is used to apply the gel to the abraded or damaged tissue site. The gel is applied so that the actively bleeding abraded or damaged area is completely covered with the resorbable molecular cross-linked gel. Suitable hemostatic agents include thrombin, fibrinogen, and other clotting factors, as described for example in U.S. Pat. Nos. 5,411,885; 4,627,879; 4,265,233; 4,298,598; 4,362,567; 4,377,572; and 4,442,655, the disclosures of which are incorporated herein by reference. Conveniently, catalytic components of the hemostasis agent, e.g. thrombin, may be combined in the syringe immediately prior to use so that their combined activities are preserved until applied to the tissue.

When used in regions surrounding nerves and other sensitive body structures, it is preferable to employ fully hydrated hydrogels (i.e. with >95% of hydration at equilibrium swell) in order to avoid damage to the nerves from swelling in an enclosed environment.

The following examples are offered by way of illustration, not by way of limitation.

EXPERIMENTAL

Example 1

Materials and Methods for Production of a Fragmented Polymeric Product

Fragmented polymeric compositions are generally prepared as follows:

Using pyrogen-free glassware and distilled water throughout, food grade gelatin (300 Bloom, Woburn Co., Woburn, Mass.) at 10% solids was allowed to swell in 0.1 N aq. sodium hydroxide and 0.05 sodium periodate and held at 0° C. to 8° C. for 2–3 days. The swollen granules were washed in distilled water until the pH reached 8. The neutralized swollen granules were dried in a laminar flow hood and re-suspended in 0.05 M sodium phosphate, 0.15 M sodium chloride, pH 7.2+/−0.2, at 10% solids. The composition was then loaded into 3.0 cc syringes and irradiated at 3.0 megarad with electron beam to sterilize.

Example 2

Materials and Methods for Production of a Fragmented Polymeric Product

Gelatin (Woburn) was allowed to swell in an aqueous buffer (e.g. 0.05 M sodium phosphate, 0.15 M sodium chloride, pH 7.2+/−0.2) at 1–10% solids and was cross-linked by either glutaraldehyde (0.01–0.05%, w/w, overnight, room temperature), by sodium periodate (0.05 M, 0° C. to 80° C., 48 hours) or by 0.3–3.0 megarads of gamma or electron beam irradiation. The gels were then extruded from a syringe using normal manual pressure.

Example 3

Materials and Methods for Production of a Fragmented Polymeric Product

Gelatin (Woburn) was allowed to swell in distilled water at 1–10% solids (w/w) chilled to 5° C. The resultant gel was fragmented by stirring with an impeller driven by a motor. Then, sodium periodate and sodium hydroxide were added and mixed to achieve 0.05 M sodium periodate and 0.10 M sodium hydroxide. The chilled mixture was held at 0° C. to 8° C. for 2–3 days. The cross-linked gel fragments were then washed with 5° C. water to achieve pH 8. Finally the gel fragments were washed with an aqueous buffer (e.g. 0.05 sodium phosphate and 0.15 sodium chloride, pH 7.2+/−0.2) and left at 0° C. to 8° C. to equilibrate with the buffer. Free buffer was decanted from the fragmented gel mass and the gel particles were loaded into syringes and irradiated at 3.0 megarads by electron beam or gamma irradiation to sterilize. Such sterilized fragmented were then extruded directly from the syringe causing further fragmentation.

Example 4

Materials and Methods for Prevention of Post Surgical Spinal Adhesions

This study demonstrated the effectiveness of the fragmented polymeric composition to prevent or reduce post-laminectomy scar formation. New Zealand White rabbits (R&R Rabbitry, Stanwood, Wash.) having weights of ≈3.0–4.0 kg were used for the study. Anesthesia was induced with an intramuscular injection of ketamine hydrochloride in combination with xylazine. Each rabbit received an injection of Baytril® intramuscularly at a dose of 5 mg/kg. The back of each rabbit was shaved from the level of the mid thorax (≈T-10) to the tail. The shaved area was extended far enough ventrally to allow for adequate skin preparation. The rabbit was placed on a circulating water heating pad in sternal recumbency. A small towel was placed ventral to the abdomen to produce a slight lumbar flexion. The skin of the lumbosacral area was prepared with an iodophor scrub and rinsed with 70% alcohol.

A midline skin incision was made from L-1 to L-5 and carried down to the lumbosacral fascia. Hemostasis was achieved with a combination of mechanical compression and electrocautery. The fascia was incised to expose the tips of the spinous processes. The paraspinous muscles were dissected free from the spinous processes and laminae of L-4 with the use of a periosteal elevator. The muscles were then held away with the use of a self-retaining retractor. A total, dorsal laminectomy of L-4 was performed by removal of the spinous process with rongeurs and careful excision of the lamina to the base of the mammillary process bilaterally.

Care was taken to avoid injury to the spinal cord or cauda equina. The laminectomy defect was irrigated with sterile saline and any remaining bone fragments were removed. The ligamentum flavum and epidural fat were removed, leaving clean dura exposed for the extent of the laminectomy.

When the procedure at the L-4 site was completed, an identical laminectomy was performed at the L-2 level. During this time, the L-4 site was protected from desiccation with gauze sponges soaked in sterile saline. The L-3 space was not manipulated to provide a soft tissue barrier between the two manipulated sites. Once both sites were prepared, the sites were treated with the test material or left as controls according to the randomized key below.

Rabbits were assigned to the experimental groups and after laminectomies were performed, the following manipulations were carried out. The exposed dura at a lumbar site was treated with 0.5–0.9 mls fragmented gelatin composition of Example 1. The material was placed in such a manner that all exposed dura was covered with the test material. The exposed dura at a different lumbar site received no treatment.

The wound was closed in layers without further irrigation. The lumbosacral fascia was closed with an absorbable suture of an appropriate size (e.g. 4-0), in a simple interrupted pattern. The subcutaneous tissue was closed with an absorbable suture in a simple continuous pattern and the skin was closed with appropriate suture material or surgical clips.

For the first five days post-operatively, the animals received Baytril® at a dose of 5 mg/kg given intramuscularly, twice daily.

Animals were euthanized and a necropsy performed at either day 7 or day 28 post operatively. The surgical incision was dissected free and the area of laminectomy examined.

Dural adhesions were graded and scored according to extent and severity and were scored as follows:

Dural Adhesions: Connective tissue attachments between bone or deep scar and dura within the spinal canal These were evaluated by inserting a probe between the bone and dura to separate the two structures.

0 = absent, with anatomical plane evident
1 = thin adhesions
2 = moderate adhesions
3 = thick & tenacious adhesions In no case in which the fragmented gelatin composition was applied did post surgical adhesion develop. However, adhesions occurred in 71% of the control sites. The results from all animal sites tested are combined and are summarized in Table 1 below.

TABLE 1

| Site No. | Vertebral Location | Treatment | Adhesion |
|---|---|---|---|
| 1 | L4 | CONTROL/NONE | 0 |
| 2 | L1 | CONTROL/NONE | 0 |
| 3 | L3 | CONTROL/NONE | 2 |
| 4 | L4 | CONTROL/NONE | 2 |
| 5 | L4 | CONTROL/NONE | 2 |
| 6 | L2 | CONTROL/NONE | 3 |
| 7 | L2 | CONTROL/NONE | 2 |
| 8 | L1 | FRAGMENTED GELATIN COMPOSITION | 0 |
| 9 | L2 | FRAGMENTED GELATIN COMPOSITION | 0 |
| 10 | L4 | FRAGMENTED GELATIN COMPOSITION | 0 |
| 11 | L5 | FRAGMENTED GELATIN COMPOSITION | 0 |
| 12 | L5 | FRAGMENTED GELATIN COMPOSITION | 0 |

Example 5

Vessel Plug

This study demonstrated the effectiveness of the fragmented polymeric composition to seal a vessel puncture. The femoral artery of a farm grade Hampshire/Yorkshire cross pig (Pork Power Farms, Turlock, Calif.) was identified and cannulated using a needle (SmartNeedle™, CardioVascular Dynamics, Irvine, Calif.). After the guide wire was placed, a 9 French dilator was used to create a tunnel to the vessel and enlarge the femoral artery opening. The dilator was removed and a 7 French sheath was introduced into the femoral artery. The guide wire was then removed. Positioning was checked by withdrawing blood into the sheath side arm. Pulsatile arterial bleeding was also observed at the point of insertion of sheath at the skin incision. As the sheath was removed, a 18 gauge Teflon catheter tip attached to a hypodermic syringe was used to introduce the fragmented gelatin composition of Example 1 into the tunnel. No bleeding was observed at the point of exit demonstrating the effectiveness of the fragmented gelatin composition in sealing the vessel puncture site and surrounding tissue.

Example 6

Fragmented Polymeric Composition as a Carrier

This study demonstrated the effectiveness of the fragmented polymeric composition of Example 1 as a carrier to fill and seal a tissue divot in the liver. Three wounds (2 tissue divots and 1 tissue puncture) were induced in the liver of a farm grade Hampshire/Yorkshire cross pig (Pork Power Farms, Turlock, Calif.).

Liver tissue divot #1 was actively bleeding following the surgical creation of a tissue divot. A syringe, containing approximately 1 ml of fragmented gelatin composition containing approximately 500 U of thrombin (500 to 1000 units/ml) was extruded from a syringe and applied to completely fill the tissue defect. After 2–3 minutes, a blood clot formed causing immediate cessation of bleeding. When the applied composition was grasped with forceps, it appeared to adhere quite well to the tissue and had good integrity. The sealant was manually challenged and no additional bleeding was observed.

Liver tissue divot #2 was actively bleeding following the surgical creation of a tissue divot. Approximately 1 ml of fragmented gelatin composition containing thrombin (approximately 500 units/ml) was extruded from a syringe and applied to completely fill the tissue defect. A Rapiseal™ patch (Fusion Medical Technologies, Inc., Mountain View, Calif.) was applied using an argon beam coagulator (Valleylab, Boulder, Colo., or Birtcher Medical Systems, Irvine, Calif.). Immediate cessation of bleeding occurred.

Liver puncture #1, was actively bleeding following the surgical creation of a blunt puncture. Approximately 0.8 ml of fragmented gelatin composition containing thrombin (approximately 500 units/ml) was extruded from a syringe and applied to completely fill the tissue defect. Approximately 2 minutes following the delivery of the fragmented gelatin composition, all bleeding stopped.

Spleen puncture #1 was actively bleeding following the surgical creation of a blunt puncture. Approximately 0.8 ml of fragmented gelatin composition containing thrombin (approximately 500 units/ml) was extruded from a syringe and applied to completely fill the tissue defect. Approximately 2 minutes following the delivery of the fragmented gelatin composition, all bleeding stopped.

In the above four examples, the delivery system used was a 3 cc syringe (Becton Dickinson, Franklin Lakes, New Jersey). It contained the fragmented gelatin composition of example 1.

A material according to the present invention for filling tissue divots and other defects could be prepared as follows. A thrombin solution (0.5 ml; 4,000 to 10,000 U/ml) is added to 4.5 ml of flowable gel to produce 5 ml of gel containing 400 to 1000 U/ml thrombin. The gel can be used in any convenient amount, e.g. 0.5 ml to 5 ml.

Example 7

Fragmented Polymeric Composition as a Tissue Filler and Anastomic Sealant

This study demonstrated the effectiveness of the fragmented gelatin composition as a wound closure system that fills and seals tissue defects. Four tissue divots were surgically induced, 1 in the lung, 2 in the liver and 1 in the spleen of a farm grade Hampshire/Yorkshire cross pig (Pork Power Farms, Turlock, Calif.).

On the lung, following the surgical creation of the tissue divot, an air leak was observed. Approximately 1 ml of the fragmented gelatin composition of Example 1 was extruded from a syringe and applied to completely fill the tissue defect. A Rapiseal™ patch (Fusion Medical Technologies, Inc., Mountain View, Calif.) was applied using an argon beam coagulator (Valleylab, Boulder, Colo., or Birtcher Medical Systems, Irvine, Calif.). Immediate cessation of the air leak occurred. When the applied patch was grasped with forceps, it appeared to adhere quite well to the tissue and had good integrity. The fragmented gelatin composition was challenged by ventilating the lung to a pressure of 28 cm water. No air leak was observed.

On the liver, following the surgical creation of the tissue divot, excessive bleeding was observed. Approximately 1 ml of fragmented gelatin composition was extruded from a syringe and applied to completely fill the tissue defect. The fragmented composition swelled and adequately stopped the bleeding although some seepage bleeding was observed.

On the liver, following the surgical creation of the tissue divot, excessive bleeding was observed. Approximately 1 ml of fragmented gelatin composition was extruded from a syringe and applied to completely fill the tissue defect. A Rapiseal™ patch (Fusion Medical Technologies, Inc., Mountain View, Calif.) was applied using an argon beam coagulator (Valleylab, Boulder, Colo., or Birtcher Medical Systems, Irvine, Calif.). Immediate cessation of the bleeding occurred. When the applied patch was grasped with forceps, it appeared to adhere quite well to the tissue and had good integrity.

Spleen puncture #1 was actively bleeding following the surgical creation of a blunt puncture. Approximately 0.8 ml of fragmented gelatin composition was extruded from a syringe and applied to completely fill the tissue defect. Approximately 2 minutes following the delivery of the fragmented gelatin composition, all bleeding stopped.

A female juvenile farm grade goat (Clovertop Dairy, Madera, Calif.) was used under appropriate anesthesia. The right cartoid artery was exposed. The vessel was carefully dissected to remove any connective tissue. The vessel was clamped using atraumatic vascular clamps, separated by a distance of approximately 2–3 cm. The vessel was dissected using a standard scalpel blade to expose 2 free vessels ends. An end-to-end anastomosis was created using 6-0 prolene suture in an interrupted fashion. Following completion of the anastomoses, the clamps were released. Bleeding was observed at the anastomotic site. Approximately 2 cc of the fragmented gelatin composition containing thrombin (approximately 500 units/ml) was extruded from a syringe around the anastomoses. Gauze was placed against the composition. Approximately 3 minutes after the application of the fragmented gelatin composition, all bleeding was observed to have ceased. The incision was appropriately closed and the animal was allowed to recover for subsequent follow-up.

Example 8

Materials and Methods for Prevention of Post Surgical Abdominal Adhesions

This study demonstrated the effectiveness of the fragmented gelatin composition in preventing/reducing the incidence of adhesions in the abdominal cavity when used alone or in conjunction with the RapiSeal™ patch (Fusion Medical Technologies, Inc., Mountain View, Calif.).

A standard animal model for evaluating surgical adhesions has been developed using the Sprague Dawley rat (Harris, E. S. (1995) "Analysis of the kinetics of peritoneal adhesion formation in the rat and evaluation of potential anti-adhesive agents," *Surgery* 117:663–669). In this model, a single, specific adhesion may be objectively measured.

For this study, 15 Sprague Dawley rats were used. Anesthesia was induced with an intramuscular injection of ketamine hydrochloride in combination with xylazine. Following anesthesia and appropriate preparation for surgery, a midline was performed. A defect in the abdominal bodywall was created approximately 1 cm lateral to the midline incision. The defect was created by excising a 1×2 cm segment of parietal peritoneum, including s superficial layer of muscle. A 1×2 cm defect was then created on the serosal surface of the cecum. The cecum was abraded by scraping with a scalpel blade so that a homogeneous surface of petechial hemorrhage was created over the abraded surface. The cecum was then elevated and positioned so that at closure, the cecum would contact the abdominal wall defect. The abdominal wall defect was similarly abraded. Both abraded areas were exposed to air for 10 minutes.

The following 3 experimental groups were established. Each group had 5 animals.
Group 1: Control/No treatment prior to closure
Group 2: Fragmented gelatin composition of Example 1
  Placed between abdominal wall and cecum defects prior to closure.
Group 3: Fragmented gelatin composition (of Example 1)+RapiSeal™ patch
  Placed on cecum defect prior to closure The midline incision was closed with 4-0 absorbable suture and the skin was closed with 4-0 silk suture. All animals were recovered from surgery and observed for 7 days.

At day 7 post-surgery, the rats were euthanized and the abdomen opened to evaluate the surgically created defect. Adhesions between the abdominal wall defect and the cecum defect, if present, were evaluated for tenacity and strength by pulling the two tissues apart. A tensiometer was used to measure the force required to break the adhesions.

Both the treatment with the fragmented gelatin composition alone and with the RapiSeal patch resulted in a reduction in the number of animals presenting with adhesions when compared to the control group. The percentage of animals in each group that had adhesions are given in the Table 2 below.

TABLE 2

| GROUP | TREATMENT | % ANIMALS WITH ADHESIONS |
|---|---|---|
| 1 | Control | 80% |
| 2 | Fragmented gelatin composition | 60% |
| 3 | Fragmented gelatin composition + RapiSeal ™ patch | 40% |

Example 9

Materials and Methods of Ascorbate Addition to Gel Prior to Irradiation

Gelatin particles (300 Bloom, Woburn Co., Woburn, Mass.) were suspended at 5%–15 by weight in methyl alcohol (Aldrich, Milwaukee, Wis.) containing 0.0%–0.1% by weight glutaraldehyde (Sigma, St. Louis, Mo.) and stirred overnight at ambient temperature. Alternatively, gelatin particles, obtained from an extract of calf hide (Spears Co., Pa.) were suspended at 5%–15% by weight in aqueous buffer at pH 9 containing 0.01%–0.1% by weight glutaraldehyde (Sigma) to form a gel that was well-mixed and refrigerated overnight. The cross-linked gelatin fragments were then rinsed three times with alcohol and dried at ambient temperature. Equilibrium swelling for the rinsed, cross-linked gelatin was then measured, and 0.5 g–1.0 g portions of this material were packed into 5 cc syringes. 3.0 ml–4.5 ml of aqueous buffer containing ascorbic acid or a salt of ascorbic acid, e.g. 0.02 M sodium phosphate (J. T. Baker, Phillipsburg, N.J.), 0.15 M sodium chloride (VWR, West Chester, Pa.), 0.005 M sodium ascorbate (Aldrich), pH 7.0, was added to the syringes containing cross-linked gelatin using a second syringe and a three-way stopcock, with care taken not to introduce extraneous air into the syringes, to form a hydrogel within several syringes. Alternatively, an aqueous buffer that did not contain ascorbic acid or a salt of ascorbic acid but was otherwise of similar composition and pH was added to other syringes containing cross-linked gelatin to form a hydrogel within them. The hydrogel-containing syringes were then gamma-irradiated under refrigerated conditions at 3.0±0.3 megarads. Equilibrium swell was measured for the hydrogel contained within the syringes after irradiation. Hydrogels that were formed using buffers that contained ascorbic acid or a salt of ascorbic acid generally maintained values for equilibrium swell upon irradiation within ±20%, and usually ±10%, of the value prior to irradiation, while gels that were formed using buffers not containing ascorbic acid or a salt of ascorbic acid experienced a decrease in equilibrium swell of 25–30% of its value prior to irradiation.

Example 10

Materials and Methods of Cross-linking and Measuring Percent Swell

Gelatin particles were allowed to swell in an aqueous buffer (e.g., 0.2 M sodium phosphate, pH 9.2) containing a cross-linking agent (e.g., 0.005–0.5% by weight glutaraldehyde). The reaction mixture was held refrigerated overnight and then rinsed three times with deionized water, twice with ethyl alcohol, and allowed to dry at ambient temperature. The dried, cross-linked gelatin was resuspended in an aqueous buffer at a low solids concentration (2–3%) at ambient temperature for a fixed period of time. Buffer was in excess of the concentration needed for equilibrium swelling, and two phases (a hydrogel phase and a buffer) were present. An aliquot of the suspension containing wet hydrogel was then filtered by applying vacuum on a 0.8 μm nominal cut-off filter membrane (Millipore, Bedford, Massachusetts). After removal of extraneous buffer, the combined weight of the retained wet hydrogel and wet filter membrane was recorded. The hydrogel and membrane were then dried at approximately 120° C. for at least two hours, and the combined weight of the dried hydrogel residue and dried filter membrane was recorded. Several measurements of samples of wet filter membrane without hydrogel residue and dried filter membrane without hydrogel were also performed and were used to deduce the net weight of wet hydrogel and dry hydrogel. "Percent swell" was then calculated as follows:

$$\text{percent swell} = 100 \times \frac{(\text{wet weight of gel} - \text{dry weight of gel})}{\text{dry weight of gel}}$$

Swell measurements were conducted in triplicate and averaged for a given sample of gelatin. The value of percent swell for samples resuspended in buffer for 18–24 hr prior to measuring wet weight was defined as "equilibrium swell."

The resulting cross-linked gelatin materials displayed equilibrium swell values in the range from 400% to 1300%. The degree of equilibrium swell depended on the method and extent of cross-linking.

Example 11

Degradation

Thirty rabbits (15 untreated control animals and 15 animals treated with fragmented gelatin composition) underwent surgery to mimic splenic injury and bleeding. A lesion on the spleen was created by making a controlled wound with a 6 mm biopsy punch. In the "Treated" group, the experimentally created injury was immediately treated with the fragmented gelatin composition to cause hemostasis of the wound. "Control" group animals were not treated during the first 7.5 minutes to demonstrate the amount of bleeding resulting from the lesion. At 7.5 minutes from the time the injury was caused, the fragmented gelatin composition was then used to stop bleeding from the lesion to prevent spontaneous exsanguination and death of the animal. All animals were allowed to recover. Ten animals each were euthanized on Days 14 and 28 post-surgery. The final necropsy date for the remaining animals was determined after the Day 28 animals were evaluated. In animals harvested at the Day 28 time point it was difficult to determine via gross examination if the test material was present or not, therefore half of the remaining animals were harvested at Day 42 and the other half at Day 56. At the time of necropsy, the site of the splenic lesion and the peritoneal cavity were evaluated macroscopically. Presence of fragmented gelatin composition in the peritoneal cavity away from the site of placement was noted and evaluated, as well as its presence or absence at the splenic lesion. The presence or absence of postoperative adhesions at the site of the splenic lesion was also evaluated and noted. The spleen was carefully dissected and processed for histological evaluation of biocompatibility and biodegradation.

The application of the fragmented gelatin composition to the surgically created wounds on the spleen resulted in good hemostatic tamponade. Following application of the fragmented gelatin composition at the time of surgery, rabbits were survived for 14, 28, 42, and 56 days postoperatively. One rabbit died of unrelated pneumonia at Day 5 postoperatively and the spleen was not harvested for histopathological examination.

At necropsy, the site of the splenic lesion as well as the peritoneal cavity in general were evaluated grossly. Presence of the fragmented gelatin composition in the peritoneal cavity away from the site of placement was evaluated, as well as the presence or absence of the fragmented gelatin composition at the splenic lesion. The presence or absence of adhesions at the site of the splenic lesion were evaluated and noted. The spleen was carefully dissected and processed for histological evaluation.

Grossly, the site of the splenic lesion was visible in all animals, at all time points. Macroscopically, the fragmented gelatin composition was absent in two of the ten Day 14 animals. At all other time points it was not possible to identify the fragmented gelatin composition macroscopically. The macroscopic absence of the hydrogel material as measured in this rabbit model defines the degradation of the hydrogel as that term is used herein and in the claims.

In three of ten animals sacrificed at 14 days postoperatively, small amounts of the fragmented gelatin composition were found free-floating in the abdominal cavity. This most likely represents the excess material that had migrated from its placement site at the splenic lesion. In no case where this material was found away from the splenic lesion was there any evidence of tissue reaction from the visceral surfaces or the omentum. No material was found away from the site of the splenic lesion in animals that were harvested at any other time point.

No postoperative adhesions associated with the fragmented gelatin composition material were noted at the site of the splenic lesion in any animal. In all animals, as expected, there was omentum attached to the site of the splenic lesion. Other adhesions involving the spleen were rare, and when noted were incidental and usually associated with the incision of the body wall.

The fragmented gelatin composition was absent macroscopically and microscopically in two of the ten animals from the 14 day time point. At 28 days post-implant, the fragmented gelatin composition was not visible on gross observation and microscopically was completely absent in five out of ten rabbits examined and present in minimal amounts in the remaining animals, showing that the fragmented gelatin composition was composition was essentially biodegraded by 28 days. The fragmented gelatin composition was completely absent in all five animals examined at 42 days post-implant and was found in minimal amounts in only one of four rabbits examined at 56 days post-implant. Healing of the splenic wound was proceeding in a normal fashion at Day 42 and more so at Day 56.

Although the foregoing invention has been described in some detail by way of illustration and example, for purposes of clarity of understanding, it will be obvious that certain changes and modifications may be practiced within the scope of the appended claims.

What is claimed is:

1. A method for sealing a tissue tract, said method comprising at least partly filling a tissue tract with a fragmented hydrogel hydrated at less than its equilibrium swell, said fragmented hydrogel comprising subunits having sizes from 0.05 mm to 5 mm when fully hydrated and an equilibrium swell from 400% to 1300%, wherein said hydrogel degrades in the tissue tract after from 1 to 120 days.

2. A method for inhibiting bleeding at a target site in a patient's body, said method comprising delivering a fragmented hydrogel hydrated at less than its equilibrium swell, said fragmented hydrogel comprising subunits having sizes from 0.05 mm to 5 mm when fully hydrated and an equilibrium swell from 400% to 1300%, wherein said hydrogel degrades in the tissue tract after from 1 to 120 days to the target site in an amount sufficient to inhibit bleeding.

3. A method for delivering a bioactive substance to a target site in a patient's body, said method comprising delivering a fragmented hydrogel hydrated at less than its equilibrium swell, said fragmented hydrogel comprising subunits having sizes from 0.05 mm to 5 mm when fully hydrated and an equilibrium swell from 400% to 1300%, wherein said hydrogel degrades in the tissue tract after from 1 to 120 days in combination with the bioactive substance to the target site.

4. A method for delivering a swellable composition to a target site in tissue, said method comprising providing a fragmented hydrogel hydrated at less than its equilibrium swell, said fragmented hydrogel comprising subunits having sizes from 0.05 mm to 5 mm when fully hydrated and an equilibrium swell from 400% to 1300%, wherein said hydrogel degrades in the tissue tract after from 1 to 120 days, said composition being hydrated at less than its equilibrium swell and applying the composition to the target site, wherein it swells to an equilibrium swell value.

5. A method for applying a polymeric composition at a target site in a patient's body, said method comprising:

providing a biocompatible resorbable molecular cross-linked hydrogel; and extruding the gel through an orifice at the target site.

6. A method as in any of claim 1, wherein the extrusion step comprises manually dispensing the hydrogel through a syringe having an orifice size in the range from 0.01 mm to 5.0 mm.

7. A method as in any of claim 1, wherein the hydrogel has been disrupted prior to the extrusion step.

8. A method as in claim 5, wherein the target site is in tissue selected from the group consisting of muscle, skin, epithelial tissue, connective or supporting tissue, nerve tissue, ophthalmic and other sense organ tissue, vascular and cardiac tissue, gastrointestinal organs and tissue, pleura and other pulmonary tissue, kidney, endocrine glands, male and female reproductive organs, adipose tissue, liver, pancreas, lymph, cartilage, bone, oral tissue, and mucosal tissue, and spleen and other abdominal organs.

9. A method as in claim 8, wherein the target site is a void region within the selected tissue.

10. A method as in claim 9, wherein the void region is selected from the group consisting of tissue divots, tissue tracts, intravertebral spaces, and body cavities.

11. A method as in claim 9, further comprising immobilizing a barrier layer over the void after the gel has been extruded.

12. A method as in claim 5, wherein the extrusion step causes the hydrogel to fracture into sub-units having a size in the range from 0.05 mm to 3.0 mm.

13. A method as in any of claims 1–4, wherein the hydrogel is filled or delivered using a spatula, using a brush, by spraying, or manually.

14. A method as in claim 1, wherein the hydrogel has a degree of hydration in the range from 50% to 95% of the hydration at equilibrium swell.

15. A method as in any one of claims 1–4, wherein the hydrogel has been disrupted after cross-linking.

16. A method as in any one of claims 1–4, wherein the hydrogel has been disrupted before cross-linking.

17. A method as in any one of claims 1–4, wherein the hydrogel comprises a plasticizer.

18. A method as in claim 17, wherein the plasticizer is selected from the group consisting of polyethylene glycol, sorbitol, and glycerol.

19. A method as in claim 17, wherein the plasticizer is present at from 0.1% by weight to 30% by weight of the composition of the polymeric component.

20. A method as in claim 3, wherein the bioactive substance is a hemostatic agent.

21. A method as in claim 20, wherein the bioactive substance is thrombin.

22. A method as in any one of claims 1–4, wherein the hydrogel comprises a cross-linked protein hydrogel.

23. A method as in claim 22, wherein the protein is selected from the group consisting of gelatin, soluble collagen, albumin, hemoglobin, fibrogen, fibrin, casein, fibronectin, elastin, keratin, laminin, and derivatives and combinations thereof.

24. A method as in any one of claims 1–4, wherein the hydrogel comprises a cross-linked polysaccharide.

25. A method as in claim 24, wherein the polysaccharide is selected from the group consisting of glycosaminoglycans, starch derivatives, cellulose derivatives, hemicellulose derivatives, xylan, agarose, alginate, and chitosan and combinations thereof.

26. A method as in any one of claims 1–4, wherein the hydrogel comprises a cross-linked non-biologic polymer.

27. A method as in claim 26, wherein the polymer selected from the group consisting of polyacrylates, polymethacrylates, polyacrylamides, polyvinyl resins, polyactide-glycolides, polcaprolactones, polyoxyethlenes, and combinations thereof.

28. A method as in any one of claims 1–4, wherein the hydrogel comprises at least two components selected from the group consisting of cross-linked proteins, cross-linked polysaccharides, and cross-linked non-biologic polymers.

29. A method as in any one of claims 1–4, wherein the hydrogel comprises a polymer and a cross-linking agent, wherein the polymer and cross-linking agent have been reacted under conditions which yield cross-linking of polymer molecules.

30. A method as in any one of claims 1–4, wherein the molecular cross-linked hydrogel has been produced by irradiation of the polymer under conditions which yield cross-linking of polymer molecules.

31. A method as in any one of claims 1–4, wherein the molecular cross-linked hydrogel has been produced by reaction of monounsaturated and polyunsaturated monomers under conditions which yield cross-linking of polymer molecules.

* * * * *